United States Patent [19]

Hörrmann

[11] Patent Number: 4,687,783

[45] Date of Patent: Aug. 18, 1987

[54] FATTY ALDEHYDES AND ACIDS IN THE TREATMENT OF NEUROLOGICAL AND DERMATOLOGICAL DISEASES

[76] Inventor: Wilhelm Hörrmann, Staltacherstr. 34, D 8127 Iffeldorf, Fed. Rep. of Germany

[21] Appl. No.: 837,969

[22] Filed: Mar. 10, 1986

Related U.S. Application Data

[63] Continuation-in-part of Ser. No. 470,969, Mar. 1, 1983, Pat. No. 4,613,621, which is a continuation-in-part of Ser. No. 321,187, Sep. 18, 1981, abandoned, which is a continuation-in-part of Ser. No. 127,817, Mar. 6, 1980, abandoned, which is a continuation-in-part of Ser. No. 29,850, Apr. 13, 1979, abandoned, which is a continuation-in-part of Ser. No. 907,343, May 18, 1978, abandoned, which is a continuation-in-part of Ser. No. 787,902, Apr. 15, 1977, abandoned, which is a continuation-in-part of Ser. No. 682,309, May 3, 1976, abandoned, which is a continuation-in-part of Ser. No. 600,375, Jul. 30, 1975, abandoned, which is a continuation-in-part of Ser. No. 450,458, Mar. 12, 1974, abandoned, which is a continuation-in-part of Ser. No. 274,754, Jul. 24, 1972, abandoned, which is a continuation-in-part of Ser. No. 805,934, Feb. 12, 1969, abandoned, which is a continuation-in-part of Ser. No. 634,884, May 1, 1967, abandoned, which is a continuation-in-part of Ser. No. 412,862, Nov. 20, 1964, abandoned, which is a continuation-in-part of Ser. No. 211,827, Jul. 23, 1962, abandoned, which is a continuation-in-part of Ser. No. 824,798, Jul. 3, 1959, abandoned.

[51] Int. Cl.$^4$ ............................................. A61K 31/11
[52] U.S. Cl. ................................................... 514/693
[58] Field of Search ........................................ 514/693

Primary Examiner—Stanley J. Friedman

[57] ABSTRACT

This application relates to the administering of fatty aldehydes and acids to patients suffering from neurological and dermatological diseases.

1 Claim, No Drawings

FATTY ALDEHYDES AND ACIDS IN THE TREATMENT OF NEUROLOGICAL AND DERMATOLOGICAL DISEASES

CONTINUING DATA

This application is a continuation-in-part of 06/470,969 03/01/83 now U.S. Pat. No. 4,613,621 which is a continuation-in-part of 321,187 09/18/81, abandoned, which is a continuation-in-part of 06/127,817 03/06/80, abandoned, which is a continuation-in-part of 06/029,850 04/13/79, abandoned, which is a continuation-in-part of 05/907,343 05/18/78, abandoned, which is a continuation-in-part of 05/787,902 04/15/77, abandoned, which is a continuation-in-part of 05/682,309 05/03/76, abandoned, which is a continuation-in-part of 05/600,375 07/30/75, abandoned, which is a continuation-in-part of 05/450,458 03/12/74, abandoned, which is a continuation-in-part of 05/274,754 07/24/72, abandoned, which is a continuation-in-part of 04/805,934 02/12/69, abandoned, which is a continuation-in-part of 04/634,884 05/01/67, abandoned, which is a continuation-in-part of 04/412,862 11/20/64, abandoned, which is a continuation-in-part of 04/211,027 07/23/62, abandoned, which is a continuation-in-part of 03/824,798 07/03/59, abandoned.

INTRODUCTION AND LIST OF INDICATION

Certain neurological diseases, namely shaking paralysis and schizophrenia, are according to applicants invention caused by different disorders in the body's own lipid system, namely that of certain fatty aldehydes and acids.

Certain dermatological diseases on the other side are caused by microorganism. Such microorganism needs for their becoming effective—that is illness generating—a specific predisposition of the affected body. In case of syphilis and acne vulgaris these predispositions are produced according to applicants invention by disorders of the body's own lipid system namely that of aldehydes and fatty acids. Therefore subject of this invention is the treating of syphilis or acne vulgaris and the treating of shaking paralysis or schizophrenia.

CHEMISTRY

The compounds of the invention are aliphatic unsaturated compounds. They are unbranched. They are fatty acids and aldehydes. Structural formulae for the compounds are set forth below. The geometric isomero are indicated by "cis" and "trans" notation, and the optical isomers are indicated by $\alpha$ and $\beta$ notation.

STRUCTURAL FORMULAS OF THE SUBSTANCES

Structural Formulas of the substances (1) $OHC\ (CH_2)_4 CH=CH\ (CH_2)_4\ CH_3$
 cis (2) $OHC\ (CH_2)_4 CH=CH\ (CH_2)_4 CH_3$
 trans (3) $OHC\ (CH_2)_6 CH=CH\ (CH_2)_6\ CH_3$
 cis (4) $OHC\ (CH_2)_6 CH=CH_2)_6\ CH_3$
 trans (5) $HOOC\ (CH_2)_6 CH=CH\ (CH_2)_6\ CH_3$
 cis (6) $HOOC\ (CH_2)_6 CH=CH\ (CH_2)_6\ CH_3$
 trans (7) $OHC\ (CH_2)_4 CH=CH\ (CH_2)_4\ CH=CH\ (CH_2)_4\ CH_3$
 cis    cis (8) $OHC\ (CH_2)_4 CH=CH\ (CH_2)_4\ CH=CH\ (CH_2)_4\ CH_3$
 trans   cis (9) $OHC\ (CH_2)_4\ CH=CH\ (CH_2)_4\ CH=CH\ (CH_2)_4\ CH_3$
 cis    trans

(10) $OHC\ (CH_2)_4\ CH=CH\ (CH_2)_4\ CH=CH\ (CH_2)_4\ CH_3$
 trans   trans

(11) OH
$OHC\ C\ (CH_2)_5\ CH=CH\ (CH_2)_6\ CH=CH\ (CH_2)_6\ CH_3$
 H
 alpha   cis       cis

(12) OH
$OHC\ C\ (CH_2)_5\ CH=CH\ (CH_2)_6\ CH=CH\ (CH_2)_6\ CH_3$
 H
 alpha   trans      cis

(13) OH
$OHC\ C\ (CH_2)_5\ CH=CH\ (CH_2)_6\ CH=CH_2)_6\ CH_3$
 H
 alpha   cis       trans

(14) OH
$OHC\ C\ (CH_2)_5\ CH=CH\ (CH_2)_6\ CH=CH\ (CH_2)_6\ CH_3$
 H
 alpha   trans      trans

(15) H
$OHC\ C\ (CH_2)_5\ CH=CH\ (CH_2)_6\ CH=CH\ (CH_2)_6\ CH_3$
 OH
 beta    cis       cis

(16) H
$OHC\ C\ (CH_2)_5\ CH=CH\ (CH_2)_6\ CH=CH\ (CH_2)_6\ CH_3$
 OH
 beta    trans      cis

(17) H
$OHC\ C\ (CH_2)_5\ CH=CH\ (CH_2)_6\ CH=CH\ (CH_2)_6\ CH_3$
 OH
 beta    cis       trans

(18) H
$OHC\ C\ (CH_2)_5\ CH=CH\ (CH_2)_6\ CH=CH\ (CH_2)_6\ CH_3$
 OH
 beta    trans      trans

(19) OH
$HOOCC\ (CH_2)_5\ CH=CH\ (CH_2)_6\ CH=CH\ (CH_2)_6\ CH_3$
 H
 alpha   cis       cis

(20) OH
$HOOCC\ (CH_2)_5\ CH=CH\ (CH_2)_6\ CH=CH\ (CH_2)_6\ CH_3$
 H
 alpha   cis       trans

(21) OH
$HOOCC\ (CH_2)_5\ CH=CH\ (CH_2)_6\ CH=CH\ (CH_2)_6\ CH_3$
 H
 alpha   trans      cis

-continued

Structural Formulas of the substances

(22)   $\underset{\text{alpha}}{\text{HOOCC (CH}_2)_5} \underset{H}{\overset{OH}{\text{CH}}}=\text{CH (CH}_2)_6 \underset{\text{trans}}{\text{CH}=\text{CH}} (\text{CH}_2)_6 \text{CH}_3$
   alpha       trans       trans

(23)   HOOCC (CH$_2$)$_5$ $\overset{H}{\underset{OH}{\text{CH}}}$=CH (CH$_2$)$_6$ CH=CH (CH$_2$)$_6$ CH$_3$
   beta        cis         cis

(24)   HOOCC (CH$_2$)$_5$ $\overset{H}{\underset{OH}{\text{CH}}}$=CH (CH$_2$)$_6$ CH=CH (CH$_2$)$_6$ CH$_3$
   beta        cis         trans

(25)   HOOCC (CH$_2$)$_5$ $\overset{H}{\underset{OH}{\text{CH}}}$=CH (CH$_2$)$_6$ CH=CH (CH$_2$)$_6$ CH$_3$
   beta        trans       cis

(26)   HOOCC (CH$_2$)$_5$ $\overset{H}{\underset{OH}{\text{CH}}}$=CH (CH$_2$)$_6$ CH=CH (CH$_2$)$_6$ CH$_3$
                trans       trans

DERIVATIVES OF THE COMPOUNDS

Aldehydes may occur in free form or bound, as an enolic or acetalated substance.

Typical examples are the enol ethers with alcohol group bearing substances for example ethanol or glycerol.

Typical examples for the acetalated form are diethylacetales or glycerol-acetales of the aldehydes.

Derivatives of the acids are the salts and the esters.

Typical examples are the natrium-, kalium- or calcium salts and the ethanol or glycerol esters or the esters with other hydroxyl-group bearing substances, also acid amino compounds of the sphingolipid type.

Other derivatives of fatty aldehydes and acids are the lipids especially those containing glycerol, sphingosin, kolamin, cholin, phosphat, hexoses and the like. Important derivatives of fatty aldehydes and acids are the plasmalogens.

Further pharmaceutical examples for both fatty aldehydes and fatty acids are the ethers of the aldehydes and the esters of the acids with physiologic acids of bile.

HOW TO MAKE THE INVENTION

The synthesis of the claimed fatty aldehydes and acids and their derivatives can be performed in different ways all well known to chemistry and biochemistry. Examples are given in the published U.S. Pat. No. 4,239,756.

HOW TO USE THE INVENTION

It is preferred to administer the compounds in form of mixtures containing their isomers in equimolar amounts. For practical reasons the compounds are separated in two groups of isomers:

group I isomers, of
 6-n-docenoic aldehyde
 8-n-hexadecenoic aldehyde and
 8-n-hexadecenoic acid group II isomers of
 6,12-n-octadecadienoic aldehyde
 8,16-n-tetracosadienoic-2-hydroxy aldehyde and
 8,16-n-tetracosadienoic-2-hydroxy acid.

Group I is indicated in cases of syphilis, which is augmented by the additional administering of group II too. Though it would be sufficient in syphilis to give only cis or trans isomers of the compounds, it may be more practical for chemical and medical reasons to use all the isomers. In some cases of shaking paralysis(morbus Parkinson) and in schizophrenia and in Acne vulgaris (as in leprosy) it is sufficient to administer only group II of the isomers.

Dosage for group I is pro die 50–200 mg/kg of the mixture. The dosage is the same for group II. Dosages are general mean values and may be raised, if necessary. Dosages relate to the free compounds.

While parenteral administration should be restricted to emergency cases, the preferred way of administering is the oral one as compounds per se or derivatives combined with glycerol, bile acid, plasmalogen and the like.

The compounds may be diluted in plant oils, enclosed in capsules and mixed in emulsions.

The total dosage per day must not be given in one single dose but in several doses distributed over the day. Being a substitution therapy the administration must be continued over long periods of time.

What is claimed is:

1. A method of treating shaking paralysis or schizophrenia in a patient having shaking paralysis or schizophrenia administering to that patient 100–400 mg/kg daily of at least one of the geometric and optical isomers of
 6-n-dodecenoic aldehyde
 8-n-hexadecenoic aldehyde and
 6, 12-n-octadecadienoic aldehyde or
 8, 16-n-tetracosadienoic-2-hydroxy aldehyde or
 8, 16-n-tetracosadienoic-2-hydroxy acid
per se or as an ether or ester of ethanol or physiologic acid of bile or in form of lipid especially plasmalogen said isomer being diluted in plant oils or in the form of capsule or emulsion.

* * * * *